United States Patent [19]

Powers

[11] Patent Number: 4,607,642

[45] Date of Patent: Aug. 26, 1986

[54] UNALIASED QUADRATURE AUDIO SYNTHESIZER

[75] Inventor: Jeffry E. Powers, Bainbridge Island, Wash.

[73] Assignee: Advanced Technology Laboratories, Bothell, Wash.

[21] Appl. No.: 601,816

[22] Filed: Apr. 19, 1984

[51] Int. Cl.[4] ............................................ A61B 10/00
[52] U.S. Cl. .................................. 128/663; 73/861.25
[58] Field of Search ...................... 128/663; 73/861.25

[56] References Cited

PUBLICATIONS

Hoeks, A. P. G., "On The Development of a Multi-Gate Pulsed Doppler System with Serial Data Processing", Thesis, U. of Linburg, Netherlands, presented 5 Mar. 1982.

Primary Examiner—Kyle L. Howell
Assistant Examiner—Francis J. Jaworski
Attorney, Agent, or Firm—Lawrence S. Levinson; Sanford J. Asman

[57] ABSTRACT

The apparatus described unaliases a Doppler signal which is related to the velocity of blood flowing in a sample volume. It then generates an audio output corresponding to the unaliased Doppler signal. The device generates an unaliased, instantaneous signal which corresponds to the Doppler frequency associated with the blood velocity in the sample volume. That unaliased instantaneous frequency is fed into programmable read only memories (PROMs) which provide digitized values for the sine and cosine functions. Those values are fed into digital-to-analog converters, and they are scaled to provide audio outputs.

4 Claims, 8 Drawing Figures

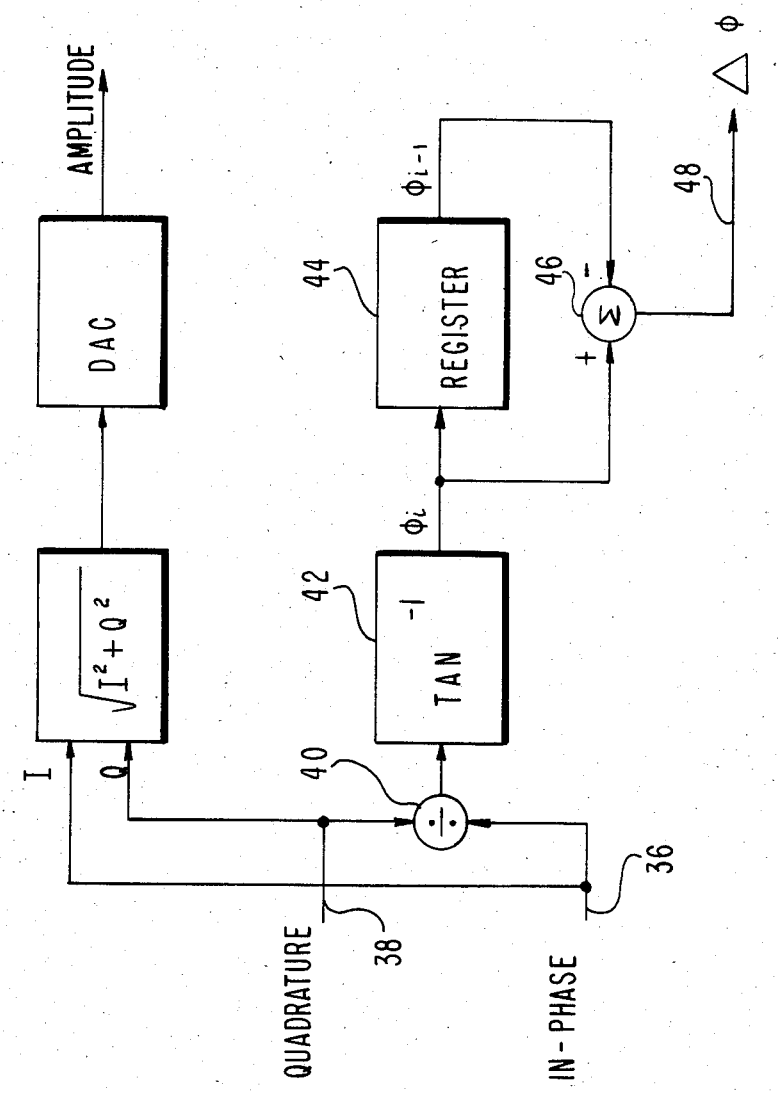

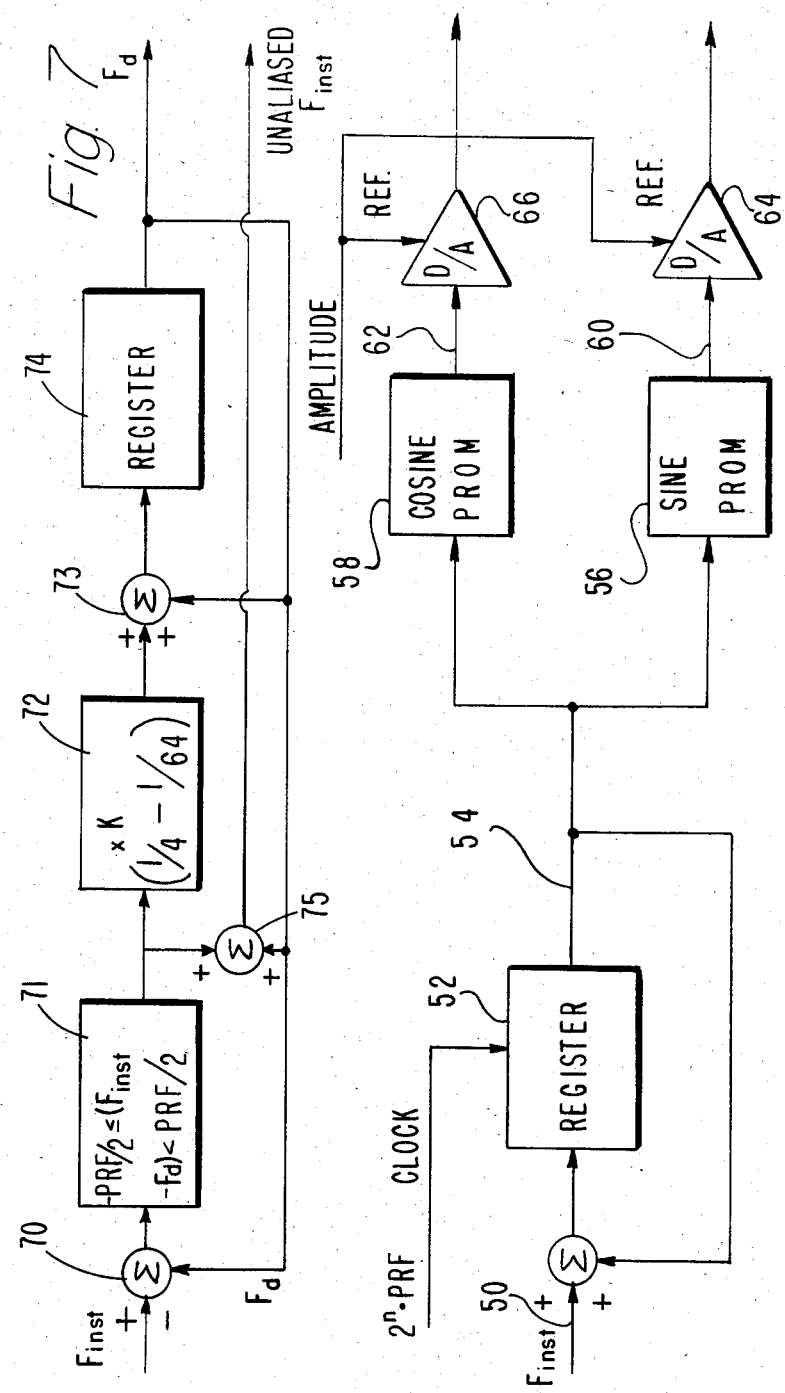

UNALIASED QUADRATURE AUDIO SYNTHESIZER

BACKGROUND OF THE INVENTION

The present invention relates to medical ultrasound diagnostic equipment. In particular it relates to a Doppler blood velocity meter.

In the measurement of blood velocity using pulsed ultrasound Doppler equipment, there is a recognized problem in measuring the velocity of blood in deep lying vessels. The problem results from the fact that the pulse repetition frequency is determined, in part, by the depth within the body of the blood whose velocity is being measured. The pulse repetition frequency is typically selected such that a pulse can be transmitted from the transducer and reflected from blood flowing within the vessel with the return pulse being received prior to the transmission of the next succeeding pulse.

As used herein, the term "PRF" means the pulse repetition frequency, and the term "sample volume" means the region of interest of blood flow velocity. These terms are well known and understood in the art. As will be recognized by those skilled in the art, the maximum PRF which can be used without introducing depth ambiguities is equal to the speed of sound in the medium divided by twice the depth of the sample volume. A phenomenon which has been observed and which is well recognized, called "aliasing", occurs when blood flow exceeds a maximum velocity for a given ultrasound transmitted frequency. This results from the fact that the Doppler shift frequency is equal to twice the ultrasound transmitted frequency times the velocity of the moving blood divided by the velocity of sound in the body times the cosine of the angle between the moving blood and the insonifying sound wave. When the Doppler frequency is more than one half the PRF, the phenomenon of aliasing, wherein the blood flow appears to have a different velocity or direction then it actually has, will be observed. The aliasing phenomenon occurs when the maximum blood flow velocity is greater than or equal to the square of the speed of sound in the human body divided by product of eight times the ultrasound transmitted frequency times the sample volume body times the cosine of the angle between the moving blood and the insonifying sound wave. In other words, a maximum velocity of blood flow which can be measured without exhibiting aliasing is inversely proportional to the sample volume depth in the body for a given ultrasound transmitted frequency.

While one approach to increasing the maximum velocity which can be measured without aliasing is to reduce the frequency of the ultrasound transmitted energy, if the frequency decreases below about 2 MHz, the scattering phenomenon, which is required for observing the returned Doppler signals, is degraded. In addition, a reduction in the ultrasound transmitted frequency reduces also the resolution of the sample volume. Accordingly, while the approach of decreasing the frequency of the ultrasound transmitted frequency can be helpful to about 2 MHz, thereafter it has been found not to be a desirable approach to use for eliminating the aliasing effect. Accordingly, a new approach to providing an unaliased signal would be desirable.

SUMMARY OF THE INVENTION

In accordance with the present invention an apparatus is described which unaliases a Doppler signal and then generates an audio output of the unaliased Doppler signal which corresponds to the blood velocity. The invention is comprised of means for generating an unaliased instantaneous frequency corresponding to the Doppler frequency associated with the blood velocity in the sample volume. The unaliased instantaneous frequency is fed into programmable read only memories (PROMs) which provide digitized values for the sine and cosine functions. Those values are fed into digital-to-analog converters and scaled to provide audio outputs.

BRIEF DESCRIPTION OF THE DRAWING

In the Drawing:

FIG. 2 is a block diagram of the Instantaneous Frequency Meter of FIG. 1;

FIG. 7 is a block diagram which illustrates the Low Pass Filter Antialiasing circuit of FIG. 1; and FIG. 8 is a block diagram of the Quadrature Frequency Synthesizer of FIG. 1.

DETAILED DESCRIPTION OF THE INVENTION

Figure 1:
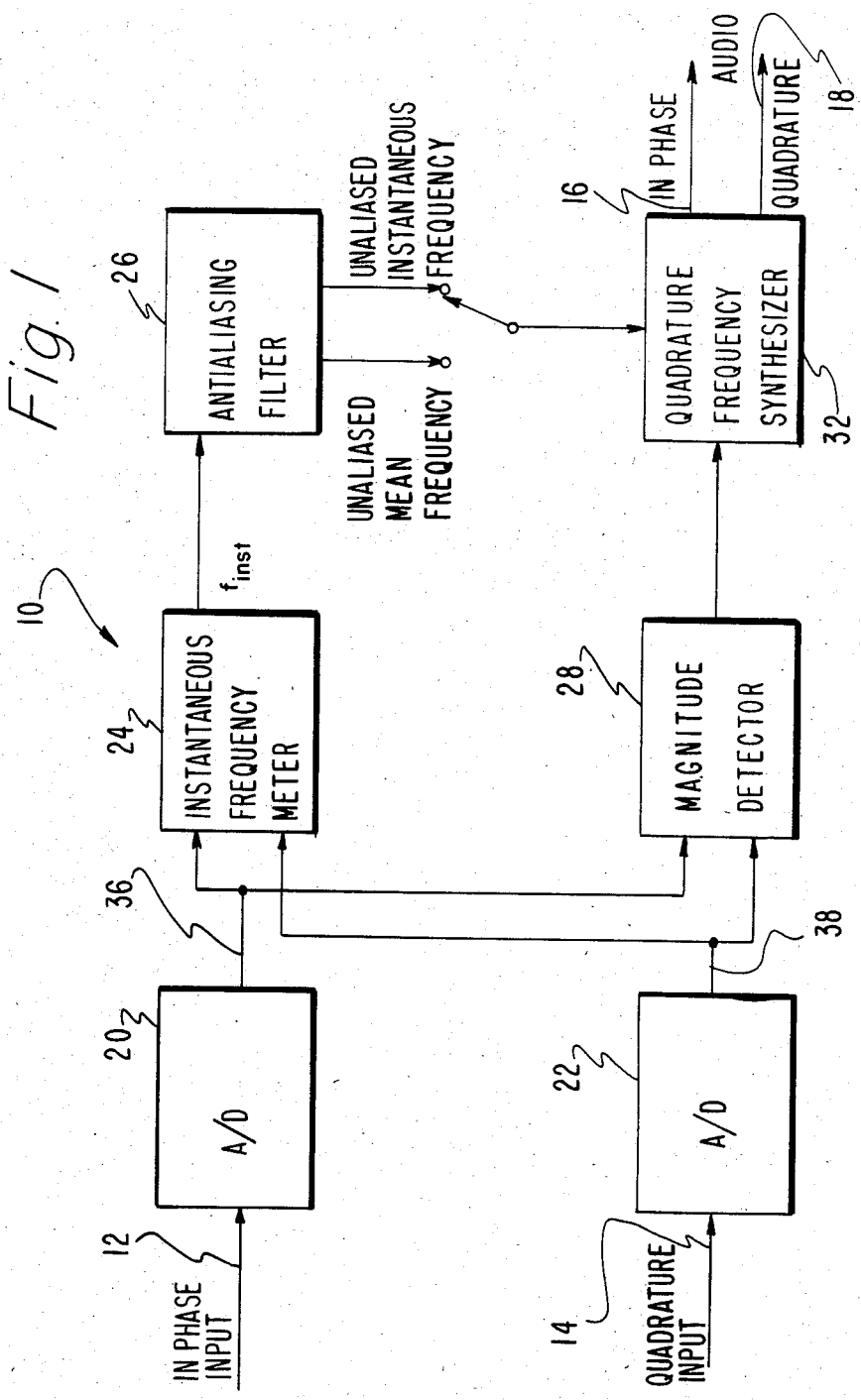
FIG. 1 is a block diagram of the present invention.

In accordance with the preferred embodiment of the invention, both in-phase and quadrature input signals, representative of the Doppler information from blood flow within the sample volume, are input into the device of the present invention. The in-phase and quadrature inputs can be derived by any of a number of commonly used techniques which are not part of the present invention. In particular, a signal can be mixed in quadrature, low-pass filtered, and digitized. These techniques are well known in the art, and one such technique is described by A.P.G. Hoeks in a thesis entitled "On the Development of a Multi-gate Pulsed Doppler System with Serial Data Processing", submitted to the University of Linburg, Maastricht, the Netherlands Referring now to FIG. 1, the present invention is an unaliasing frequency meter and audio synthesizer 10. While devices heretofore known were able to obtain the unaliased mean frequency, the mean frequency does not preserve the full spectral bandwidth of the original Doppler signal. Accordingly, an audio output merely approximated a single channel of the mean frequency which could not be used for further spectral analysis. On the other hand, the present invention recreates the unaliased instantaneous frequency which has the full spectral content of the original Doppler signal when resynthesized into quadrature audio output. Accordingly, further spectral analysis can be performed, which includes the ability to determine positive or negative frequency shifts, corresponding to flow direction.

As shown, the invention is designed to take both in-phase and quadrature inputs on input lines 12, 14, respectively, and provide both in-phase and quadrature audio outputs on output lines 16, 18, respectively. In accordance with the invention, the input signals on lines 12, 14 are fed into analog-to-digital converters (ADCs) 20, 22, respectively. The outputs from the ADCs 20, 22 are fed into an instantaneous frequency meter 24 whose output is the instantaneous frequency, $f_{inst}$, is fed into an antialiasing filter 26, whose outputs are the unaliased mean frequency and the unaliased instantaneous frequency.

The digitized outputs of the ADCs 20, 22 are also fed into a magnitude detector 28 prior to being fed into a quadrature frequency synthesizer circuit 32. The quadrature frequency synthesizer circuit 32 also receives, as an input, either the unaliased mean frequency or the unaliased instantaneous frequency from the antialiasing filter 26. The outputs of the quadrature frequency synthesizer circuit 32 are the in-phase and quadrature audio signals on output lines 16, 18, respectively.

Referring now to FIG. 2, the manner in which the instantaneous frequency, $f_{inst}$, is determined will be described. In particular, the in-phase and quadrature input signals which leave the ADCs 20, 22 on lines 36, 38, respectively (shown in FIG. 1), are fed into a divider 40. The output of the divider 40 is fed into an arc tangent circuit 42 whose output is $\phi_i$.

This value, $\phi_i$, is stored in register 44 for one PRF cycle and is then subtracted from the instantaneous phase, $\phi_i$, in subtractor 46 to get the change in phase that occurred during one PRF interval, i.e., $\Delta\phi = \phi_i - \phi_{i-1}$ on line 48. Since the instantaneous frequency, $f_{inst}$, is the derivative of instantaneous phase, i.e., $\phi_i/dt$, we have an estimate of instantaneous frequency, as $f_{inst} = \Delta\phi/\Delta T$. Since $\Delta T = 1/PRF$, $f_{inst} = (\Delta\phi)(PRF)$.

In order to obtain a mean frequency estimate, the instantaneous frequency, $f_{inst}$, must be filtered. But, even if the true Doppler frequency does not alias, the detected instantaneous frequency has a wide range of values, some of which appear to alias.

Figure 3:
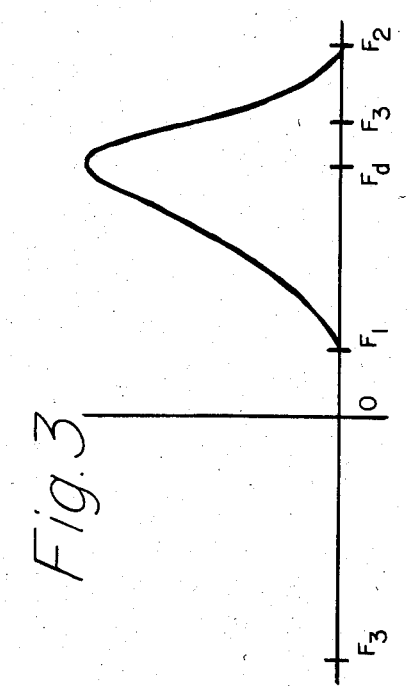
FIG. 3 is a spectrum of frequencies showing Doppler shift frequencies which are present in the system.

With reference to FIG. 3 herein, if no aliasing took place, Doppler shift information would be provided as a spectrum of Doppler frequencies which extend beyond the frequency at which aliasing occurs. As shown in FIG. 3, the spectrum of the Doppler frequencies, absent aliasing, extends from a first frequency, $F_1$, through a second frequency, $F_2$, beyond a third frequency, $F_3$, where $F_3$ is equal to PRF/2, the frequency at which aliasing occurs. As a consequence of aliasing, any frequencies lying between $F_3$ and $F_2$ are shifted downward in the frequency spectrum by a frequency equivalent to PRF, giving the actual aliased Doppler frequency spectrum shown in FIG. 4. As shown, the actual spectrum has two portions. A first portion extends from frequency $F_1$ to frequency $F_3$, i.e. PRF/2 and the second portion extends from $-F_3$ to $F_2 - PRF$.

Figure 4:
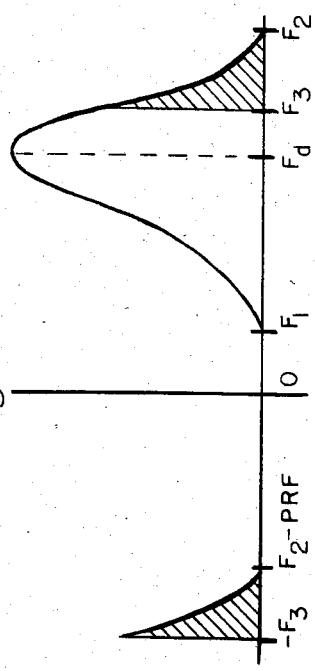
FIG. 4 is a spectrum of frequencies showing actual aliased Doppler frequencies.
Figure 5:
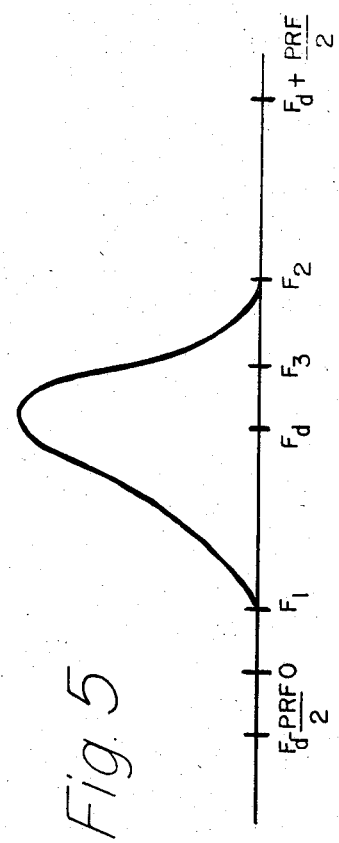
FIG. 5 is a spectrum of regenerated frequencies.

In accordance with the present invention, the approach to regenerating the spectrum of FIG. 3 from FIG. 4 involves defining a floating reference interval for detecting the mean frequency. Normally, frequency reference intervals are centered about zero, as shown in FIG. 3. The present invention uses a method which centers the reference interval about the detected mean frequency, $F_d$, as shown in FIG. 5, and thus the present system can track the mean frequency, $F_d$, even though it aliases very badly.

Figure 6:
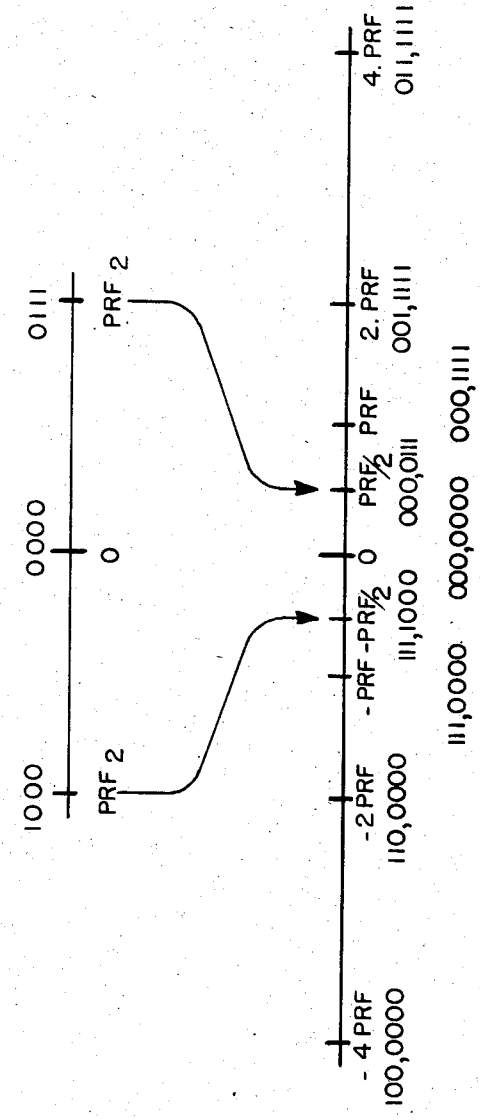
FIG. 6 is an illustration of the digital representation of frequencies.

Since the measured instantaneous frequency was only defined from $-PRF/2$ to $+PRF/2$, in a digital signal processor of the present type, extra bits must be added to extend the range of unaliased frequencies. To track from $-4PRF$ to $+4PRF$ requires three extra bits, as shown in FIG. 6. In general, n extra bits will give frequencies defined on the interval $-2^{(n-1)} \times PRF$ to $+2^{(n-1)} \times PRF$. What is required, then, is to place the measured instantaneous frequency within the new reference interval between $F_d - PRF/2$ and $F_d + PRF/2$. This is accomplished by subtracting the mean Doppler frequency, $F_d$, from the instantaneous frequency, $F_{inst}$, and forcing the magnitude of the difference to be less than PRF/2 by adding or subtracting multiples of PRF. If this normalized difference is called $\Delta F_{inst}$, we have:

$$\Delta F_{inst} = F_{inst} - F_d$$

such that:

$$abs[F_{inst} - F_d] \leq PRF/2,$$

then a portion of $\Delta F_{inst}$ is added to the old mean to arrive at a new mean frequency, as shown in FIG. 7.

The manner in which this is accomplished is as follows: Without the unaliasing correction of box 71 or summation node 75, FIG. 7 represents a simple first order low pass digital filter with transfer function $H(Z) = K/(1 - (1-K)Z^{-1})$. (This is equivalent to the block diagram shown in FIGS. 5.2 and 5.4 on pages 47 and 49 of the Hoeks thesis.) The mean Doppler output $F_d$ corresponds to output $W_r(i-1)$ in Hoeks' representation.

More specifically, node 70 finds the difference between the new instantaneous frequency and the previous mean, then 72 multiplies the difference by filter constant K, which varies from about ¼ to 1/64. Thus, at node 73 we have $(F_{inst} - F_d) \times K \pm F_d$, or equivalently new $F_d = F_d(1-K) \pm K \times F_{inst}$. The output: $F_d$ is a function of the previous $F_d$ and the new $F_{inst}$. As K approaches 1, then $F_d$ is nearly equal to $F_{inst}$, or it has a high cutoff frequency. As K becomes small, $F_d$ changes very slowly, so it has a low cutoff frequency.

This describes FIG. 7 without block 71 or node 75. In this case, the reference range of the filter of FIG. 7 exactly spans the range of the input $F_{inst}$. In order to extend this range for unaliasing, extra bits are added within the filter as described earlier. If 3 extra bits are added, then $F_d$ may vary from $-4PRF$ to $\pm 4PRF$, but $F_{inst}$ only varies from $-PRF/2$ to $+PRF/2$. If one assumes that the new $F_{inst}$ cannot have changed by more than $\pm PRF/2$ from the previous means, then block 71 must be added to force the difference to be within the limits $\pm PRF/2$.

In order to produce an unaliased instantaneous frequency, summation node 75 is used. After the difference between $F_{inst}$ and $F_d$ has been forced to be within the limits $\pm PRF/2$, then that difference is added back to the mean. If $F_d$ is within the limits $\pm PRF/2$, then block 71 will have no effect, and the output of 75 will be identically $F_{inst}$. If $F_d$ is outside of this range, the output of 75 will be unaliased $F_{inst} = F_{inst} \pm n \cdot PRF$ such that $F_d - PRF \leq$ unaliased $F_{inst} < F_d \pm PRF$.

The device as described thus far, and as described more fully in the thesis by Hoeks, is a digital device which produces binary representations of the frequencies involved. As it is desirable to be able to output an audio tone which provides both in-phase audio and quadrature audio, the binary representation of instantaneous frequency must be unaliased, as was the mean in Hoeks' system, and then converted into an audio tone which has full Doppler spectral response.

In order to unalias the instantaneous frequency, $f_{inst}$, the whole normalized difference $\Delta F_{inst}$ is added to the old mean to produce a new unaliased instantaneous frequency, as shown in FIG. 7. This, then, is a binary number representing the change in phase, $\Delta\phi$, that occurred during the time interval $\frac{1}{2^n} \times PRF$. To provide an analog output, this phase change must be integrated. This is done by adding $\Delta\phi$ to itself over and over again at the rate of $2^n \times PRF$ and using the result to address look-up tables with the values of sine and cosine stored, as shown in FIG. 8.

As shown in FIG. 8, the instantaneous frequency on line 50 is entered into a register 52 whose output, on line 54, is used to address sine and cosine PROMs 56, 58. The purpose of the PROMs 56, 58 is to provide a digital look-up of the value of sine and cosine respectively for each digitized input angle on line 54. The digital outputs of the PROMs 56, 58 are fed on lines 60, 62 to digital-to-analog converters (DACs) 64, 66, respectively, to provide audio outputs as described above.

As will be understood, the sine and cosine waves are stepped through at the rate given by $f_{inst}$. If binary adders are used, and the result is computed with the same number of bits as are in the representation of $f_{inst}$, when the adder overflows, it simply starts counting through the sine wave again. It should be remembered that since new frequencies are input only once per PRF, the same value is added $2^n$ times before getting a new value. By inputting the binary numbers from the sine and cosine PROMs into DACs, an analog voltage is produced which oscillates at the rate given by $f_{inst}$. By using the amplitude of the original signal, as generated in FIG. 2, as the reference input to the DACs, then the output signals have the same amplitude fluctuations, and hence the same bandwidth, as the original signal.

I claim:

1. An unaliased quadrature audio synthesizer which preserves full spectral content of an original ultrasound Doppler signal derived from blood flow in a sample volume, which Doppler signal may include aliased frequencies, comprising:
   (a) means adapted to receive said Doppler signal and in the presence of said aliased frequencies for generating a digitized signal corresponding to the instantaneous, unaliased Doppler shift frequency resulting from blood flow in the sample volume
   (b) means for generating quadrature audio signals corresponding to said digitized signal.

2. The device of claim 1 wherein said means for generating a digitized signal corresponding to the instantaneous, unaliased Doppler shift frequency resulting from blood flow in the sample volume comprises:
   (a) means for subtracting the unaliased mean frequency from the instantaneous frequency and then adding or subtracting multiples of the PRF to obtain a resulting frequency which is greater than or equal to $-PRF/2$ and less than $PRF/2$, where PRF is the pulse repetition frequency of the Doppler transmitter; and
   (b) means for adding the unaliased mean frequency to said resulting frequency.

3. The device of claim 2 wherein said means for generating quadrature audio outputs comprises:
   (a) means for inputting the said instantaneous, unaliased Doppler shift frequency into programmable read only memories (PROMs) which hold digitized values for the sine and cosine functions;
   (b) means for stepping through said PROMs to obtain digital output values for said sine and cosine functions which correspond to the instantaneous, unaliased Doppler frequency; and
   (c) means for converting said digital output values into analog audio signals.

4. The device of claim 3 wherein said means for converting said digital output values into analog audio signals comprises:
   (a) means for detecting the magnitude of the original input signal; and
   (b) means for multiplying the binary input into the digital-to-analog converters by the amplitude of the original input signal thereby obtaining full spectral output.

* * * * *